United States Patent [19]

Nara et al.

[11] 3,931,400

[45] Jan. 6, 1976

[54] FORTIMICIN B AND PROCESS FOR PRODUCTION THEREOF

[75] Inventors: Takashi Nara, Tokyo; Seigo Takasawa, Kawasaki; Ryo Okachi, Machida; Isao Kawamoto, Machida; Mitsuyoshi Yamamoto, Machida, all of Japan

[73] Assignee: Abbott Laboratories, North Chicago, Ill.

[22] Filed: Apr. 5, 1974

[21] Appl. No.: 458,422

[30] Foreign Application Priority Data

July 23, 1973 Japan.............................. 48-42696
July 23, 1973 Japan.............................. 48-80866

[52] U.S. Cl................................... 424/118; 195/80
[51] Int. Cl.² ......................................... A61K 35/00

[58] Field of Search........................ 424/118; 195/80

[56] References Cited
OTHER PUBLICATIONS

Miller, The Pfizer Handbook of Microbial Metabolites, McGraw–Hill Book Co., Inc. N.Y., N.Y., 1961, pp. 595–596.

*Primary Examiner*—Jerome D. Goldberg
*Attorney, Agent, or Firm*—Fitzpatrick, Cella, Harper & Scinto

[57] ABSTRACT

A new antibiotic, Fortimicin B, is produced by fermentation of a microorganism belonging to the genus Micromonospora. The antibiotic is accumulated in the culture medium and is isolated therefrom.

3 Claims, 5 Drawing Figures

FORTIMICIN B AND PROCESS FOR PRODUCTION THEREOF

BACKGROUND OF THE INVENTION

The present invention relates to a new antibiotic, Fortimicin B, and a process for the production thereof. More specifically, the present invention pertains to the production of Fortimicin B by culturing a microorganism belonging to the genus Micromonospora until antibacterial activity is exhibited in the culture liquor and then isolating Fortimicin B therefrom.

Antibiotics which exhibit activity against a broad spectrum of bacteria are always in demand. To this end, a new species of microorganism has been isolated from the soil of a paddy field located in the suburbs of Hiroshima city in Hiroshima prefecture, Japan. This new species, when cultured, produces the new antibiotic, Fortimicin B, which exhibits an antibacterial activity against various Gram-positive and Gram-negative bacteria. Accordingly, the new antibiotic may be utilized for various purposes and is particularly useful as a surface disinfectant for controlling the population of Staphylococci, Escherichia and other bacteria.

SUMMARY OF THE INVENTION

Figure 1:
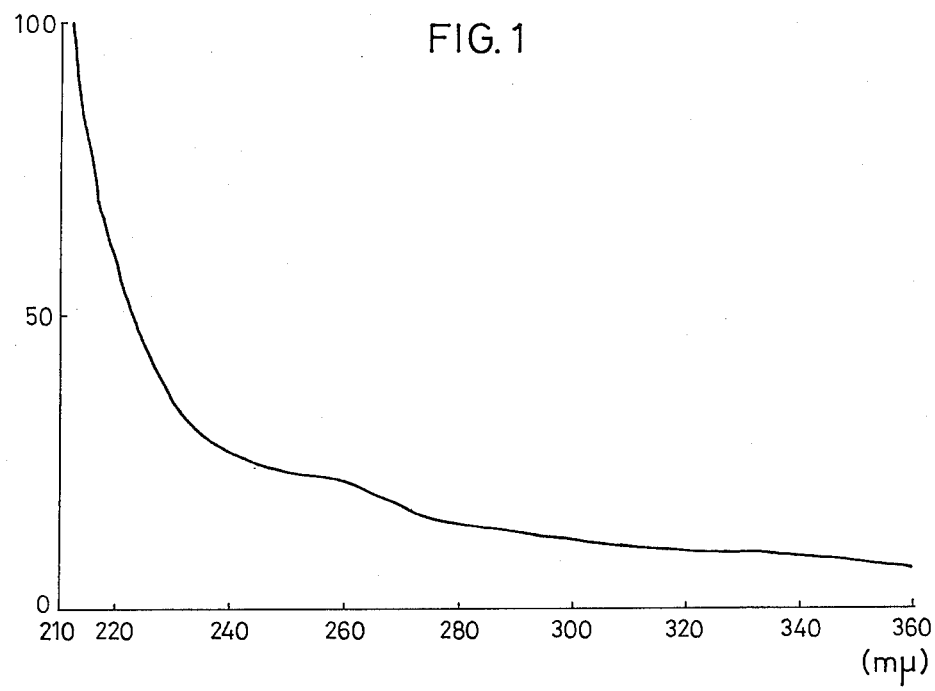
FIG. 1 is the ultraviolet absorption spectrum of Fortimicin B.

In accordance with the present invention, a new antibiotic Fortimicin B is produced by fermentation of a microorganism belonging to the genus Micromonospora which is capable of producing the antibiotic in a nutrient medium until substantial antibacterial activity is detected in the culture liquor. At the completion of culturing, the antibiotic is isolated from the culture liquor by known means such as by ion exchange resin treatment.

DESCRIPTION OF THE INVENTION

The new antibiotic of the present invention was initially identified as XK-70-A, and has now been named Fortimicin B. It is believed to have the following chemical structure:

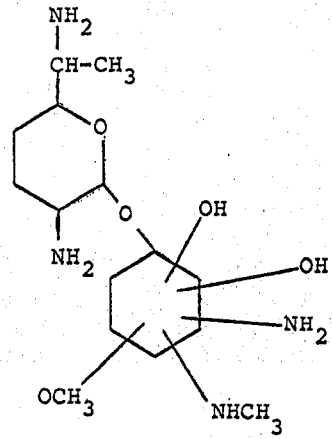

Fortimicin B is produced by fermentation of a microorganism belonging to the genus Micromonospora. A particularly suitable microorganism belongs to *Micromonospora olivoasterospora* which is a new species established by the present inventors. Its typical strain was originally identified as strain MK-70. This strain has been deposited with the American Type Culture Collection, Rockville, Maryland and has been accorded accession number ATCC 21819. The MK-70 strain has the following properties:

I. Morphology:

The MK-70 strain is Gram-positive. On conventional agar medium the MK-70 strain never forms a true aerial mycelium as observed with Streptomyces, etc. On the surface of an agar medium where there is good spore formation there is observed an olive green, wax-like and lustrous layer of spores. When the strain is cultured in a liquid medium, the culture broth shows a light wheat color in the earlier stages of culturing, but in the later stages of culturing the culture broth shows a dark olive green color and a large number of spores are observed in the culture. By microscopic observation of the cells of the MK-70 strain cultured in a liquid medium, it has been found that the mycelium is about 0.5 $\mu$ in diameter and is well developed and non-septate. A single spore is formed at the end of each sporophore (about 0.3 - 1.0 $\mu$ in length) branched from the substrate mycelium, and the spores are formed along the relatively long substrate mycelia. The matured spores are spherical and about 1.0 $\mu$ in diameter. In observing the surfaces of the spores by an electron microscope, the spores look like a star since there are a large number of projections, whose tip ends are somewhat round.

II. Culture Characteristics:

The degree of growth, surface state of colony and production of soluble pigments observed when the MK-70 strain is cultured on various media, are shown in Table 1. The color indications are given according to the classifications in the Color Harmony Manual (Container Corporation of America). Regarding the tyrosine medium, the medium described in Gordon & Smith: J. Bact. 69, 147 (1955) is used.

Table 1

| Medium | Growth | Color | Soluble pigment |
| --- | --- | --- | --- |
| Czapek's agar | Moderate Flat | Dusty olive (1 lg) | None |
| Glucose-asparagine agar | Moderate Flat, waxy | Olive (1 pl) | None |
| Nutrient agar | Good Raised, ridged | Olive (1 pl) | None |
| Egg albumin agar | Moderate Flat, waxy | Light olive drab (1 li) | None |
| Starch agar | Good Flat | Black olive teal (1 po) | None |
| Malt extract-yeast extract agar | Good Raised, ridged | Dark olive (1 pn) | Dark olive (1½ pn) |
| Oatmeal agar | Good Plicate, waxy | Amber butter-scotch (3 lc) dark brown (2 pn) | Dusty olive (1 pg) |
| Dextrose (1%) - NZ amine (3%) agar | Moderate Flat, waxy | Light wheat (2 ea) | None |
| Bennet's agar | Good Raised, ridged | Dark olive (1 pn) | None |
| Emerson's agar | Moderate Raised, ridged, waxy | Olive (1 ni) | None |

Table 1-continued

| Medium | Growth | Color | Soluble pigment |
| --- | --- | --- | --- |
| Glucose-yeast extract agar | Good Raised, ridged waxy | Dark olive (1 pn) | None |
| Peptone-iron agar | Moderate Flat, waxy | Dark Olive (1 nl) | None |
| Tyrosine agar | Moderate Flat, waxy | Olive (1 ni) | None |

III. Physiological Properties:

Physiological properties of the MK-70 strain are shown in Table 2. In the tests except those on the optimum temperature and actions upon milk and cellulose, the strain is cultured at 27°C for two weeks. The optimum temperature is determined after 5 days of culturing and the actions upon milk and cellulose are observed after one month of culturing.

Table 2

| (1) | Utilization of carbon sources: | |
| --- | --- | --- |
| | Carbon Sources: | Utilization: |
| | D-Arabinose | − |
| | D-Galactose | − |
| | D-Glucose | ++ |
| | Glycerol | − |
| | D-Lactose | − |
| | D-Fructose | − |
| | L-Inositol | − |
| | D-Mannitol | − |
| | D-Raffinose | − |
| | L-Rhamnose | − |
| | Sucrose | ++ |
| | Starch | ++ |
| | D-Xylose | − |
| (2) | Liquefaction of gelatin | Slightly positive |
| (3) | Action upon milk | Peptonized |
| (4) | Decomposition of cellulose | Slightly positive |
| (5) | Hydrolysis of starch | Positive |
| (6) | Optimum pH for growth | 6.8 − 7.5 |
| (7) | Optimum temmperature for growth | 30°C − 38°C |
| (8) | Reduction of nitrate | Positive |
| (9) | Formation of tyrosinase | Negative |
| (10) | Formation of melanoid pigments | Negative |

The MK-70 strain is a mesophile, which never forms a true aerial mycelium when cultured on an agar medium, but forms a single spore on the substrate mycelium, and it has been found by analysis that the cell wall of this strain contains meso-diaminopimelic acid. Accordingly, the MK-70 strain is regarded as a strain of the genus Micromonospora.

Reliable bases for the systematic classification of species of the genus Micromonospora have not been established. Therefore, the classification of the microorganisms of this genus has so far been conducted by an overall comparison of morphological and physiological properties, etc. There have been reported three strains belonging to the genus Micromonospora, that is, *Micromonospora echinospora* subsp. *echinospora* NRRL-2985 (ATCC 15837), *Micromonospora echinospora* subsp. *pallida* NRRL-2996 (ATCC 15838) and *Micromonospora echinospora* subsp. *ferruginea* NRRL-2995 (ATCC 15836) which exhibit blunt spines on the surface of the spore. However, these three strains of *M. echinospora* form spores of dark brown to black color when cultured on a conventional agar medium, but never show such an olive color as the MK-70 strain. The three strains of *M. echinospora* can utilize L-rhamnose, but the MK-70 strain cannot. Additionally, the three strains can produce two active substances, one of which has an activity only against Gram-positive bacteria and an Rf value of 0.4 to 0.5 in paper chromatography using water-saturated n-butanol as a developer, and the antibiotic Gentamicin having an Rf value of 0.00. On the other hand, the MK-70 strain can produce three kinds of active substances, that is, a substance having an activity only against Gram-positive bacteria and having an Rf value of 0.05 to 0.1 in paper chromatography using the aforementioned developer; a substance having an activity only against Gram-positive bacteria and having an Rf value of 0.00; and Fortimicin B, having an activity against Gram-positive and Gram-negative bacteria and having an Rf value of 0.00. As is evident from the above, the MK-70 strain is different from the three strains of *M. echinospora*.

The MK-70 strain shows an olive to dark olive color when cultured using a medium suitable for spore formation, and produces a soluble, olive pigment in some media. Among the strains of the genus Micromonospora, there are some strains capable of forming olive spores, i.e., *Micromonospora chalcea*, *Micromonospora fusca*, etc., but these are distinguished in the surface state of spores and the color of soluble pigments, etc.

Another species of Micromonospora, i.e., *Micromonospora coerulea* usually exhibits a green-blue color, and produces blue-green soluble pigments. The pigments function as an acid-base indicator and are, therefore, different from the pigment of the MK-70 strain. Moreover, the spores of *M. coerulea* are liable to disperse in a cluster state and the spore surfaces are smooth. Thus, *M. coerulea* is distinguished from the MK-70 strain.

As described above, there are no strains which correspond to the MK-70 strain among the strains of the genus Micromonospora so far reported. Therefore, the MK-70 strain is considered a new strain belonging to the genus Micromonospora and has been named *Micromonospora olivoasterospora*. The name of this species comes from the formation of olive spherical spores with projections. As stated above, the MK-70 strain has been deposited with the American Type Culture Collection as Micromonospora sp. MK-70. The MK-70 strain has also been deposited with the Fermentation Research Institute, Tokyo, Japan, and has been assigned registration number FERMP-No. 1560.

Two variant strains of *Micromonospora olivoasterospora* have also been isolated which have the ability to produce Fortimicin B. These variants differ from the type strain in that they have the ability to utilize D-galactose, D-fructose and D-xylose. One variant additionally exhibit a light wheat color when cultured on various media since they lack the ability to form spores on the mycelium. In other respects the variants closely resemble the type strain. These two variants have also been deposited with the American Type Culture Collection and have been assigned accession numbers ATCC 31009 and ATCC 31010. These variants, as well as the type strain are freely available to the public.

As is the case with other strains of Actinomycetes, the microorganisms useful in carrying out the present invention can undergo mutation by artificial means such as ultraviolet irradiation, $CO^{60}$ irradiation, X-ray irradiation and various mutation-inducing chemicals. Accordingly, any strain, even if thus mutated, is appropriate for the present invention insofar as it has the ability to produce Fortimicin B.

Generally, conventional methods for culturing microorganisms of the Actinomycetes may be employed in the process of the present invention. Thus, various nutrient sources may be employed for the culture medium. Appropriate carbon sources include glucose, starch, mannose, fructose, sucrose, molasses, etc., either alone or in combination. Additionally, hydrocarbons, alcohols, organic acids, etc., may be used depending upon the ability of utilization possessed by the particular microorganism. Inorganic and organic nitrogen sources such as ammonium chloride, ammonium sulfate, urea, ammonium nitrate, sodium nitrate, etc., and natural nitrogen sources such as peptone, meat extract, yeast extract, dry yeast, corn steep liquor, soybean meal, casamino acid, soluble vegetable protein, etc., may be used alone or in combination. In addition, such inorganic salts as sodium chloride, potassium chloride, calcium carbonate, phosphates, etc., may be added to the medium, if necessary. Furthermore, organic or inorganic materials capable of promoting growth of the microorganism and the production of Fortimicin B may be properly added to the medium.

A liquid culturing method, especially a submerged stirring culturing method, is most suitable for the present process. It is desirable to carry out culturing at a temperature of 25° to 40°C and at an approximately neutral pH. The antibiotic of the present invention is formed and accumulated in the culture liquor usually after 4 to 15 days of culturing. When the yield of Fortimicin B in the culture liquor reaches a maximum, culturing is discontinued and the antibiotic is isolated and purified from the culture liquor obtained after the microbial cells have been removed such as by filtration.

Isolation and purification of Fortimicin B from the filtrate is carried out according to the methods usually used in the isolation and purification and microbial metabolic products from culture liquor.

Since Fortimicin B is basic and is soluble in water, but poorly soluble in the ordinary organic solvents, the antibiotic can be purified by the methods usually used for the purification of so-called water-soluble basic antibiotics. More specifically, Fortimicin B may be purified by a proper combination of adsorption and desorption from cation exchange resins; column chromatography using cellulose; Sephadex LH-20(trade name, produced by Pharmacia Fine Chemicals Inc., U.S.A.); silica gel chromatography and the like methods.

For example, the cell-free culture filtrate is first adjusted to a pH of 7.5, and then subjected to adsorption on a cation exchange resin, Amberlite (trade name, produced by Rohm and Haas Co., U.S.A.) IRC-50 ($NH_4^+$ form). After washing with water, elution is carried out with 1N aqueous ammonia. The active fraction is concentrated under reduced pressure and then passed through a column of anion exchange resin, such as Dowex (trade name, produced by Dow Chemical Co., U.S.A.) 1×2 ($OH^-$ form). The adsorbed substances are eluted with water, and the eluted active fractions are collected and concentrated under reduced pressure, whereby a crude powder containing Fortimicin B and other active components is obtained.

Silica gel chromatography, for example, is used as a method for isolating Fortimicin B from the crude powder. As a developer, the lower layer of a mixture of chloroform, isopropanol and 17% aqueous ammonia (2:1:1) is used. More specifically, the crude powder is dissolved in the developing solvent, introduced into a column of silica gel and developed with the same solvent. The first active fraction contains Fortimicin B. Other active components such as a substance tentatively identified as XK-70-1, are contained in successively eluted fractions. The fractions containing Fortimicin B are collected and concentrated under reduced pressure. After freeze-drying the concentrate, a white powder comprising the base of the antibiotic is obtained.

The active fractions containing Fortimicin B are determined by ascending chromatography using Whatman No. 1 filter paper. Development is carried out at room temperature for 10 to 15 hours using the lower layer of a solvent mixture of chloroform, methanol and 17% aqueous ammonia (2:1:1). The Rf value of Fortimicin B on the paper chromatogram is about 0.65.

Fortimicin B is a white basic powder having a molecular weight of 348 and a melting point from 101° - 103°C. The elementary analytical values are found to be C = 51.72%, H = 9.20%, N = 16.16% and O = 22.92%. The molecular formula is considered to be $C_{15}H_{32}N_4O_5$.

FIG. 1 illustrates the ultraviolet absorption spectrum of an aqueous solution of Fortimicin B. The spectrum reveals no characteristic maximum ultraviolet absorption between 220 and 360 m$\mu$, and shows simply a terminal absorption.

The optical rotation of the free base of Fortimicin B is $[\alpha]_D^{24} = +22.2$ (C = 1.01, $H_2O$).

Figure 2:
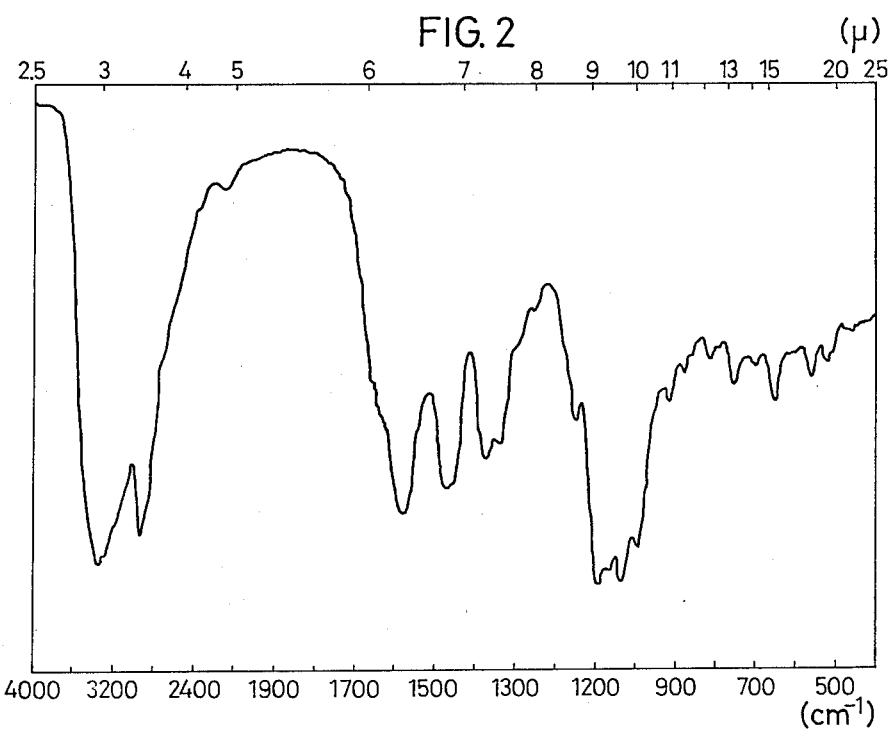
FIG. 2 is the infrared absorption spectrum of Fortimicin B.

FIG. 2 illustrates the infrared absorption spectrum of the antibiotic (KBr tablet). As is apparent from the figure, Fortimicin B shows peaks at the following wavelengths ($cm^{-1}$):

523, 561, 650, 702, 755, 815, 879, 917, 993, 1034, 1066, 1093, 1150, 1250, 1336, 1370, 1470, 1578, 2100, 2930 and 3355

Figure 3:
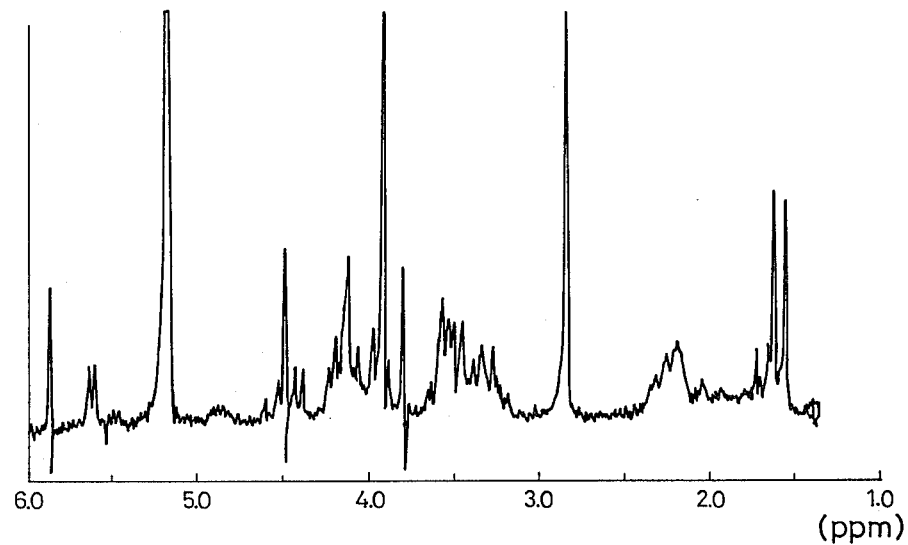
FIG. 3 is the nuclear magnetic resonance spectrum of Fortimicin B.

The nuclear magnetic resonance (NMR) spectrum of Fortimicin B is illustrated in FIG. 3. As is apparent from the spectrum, the absorption at 5.62 ppm based on an anomeric proton suggests the presence of a monoglycoside in the antibiotic. The spectrum further illustrates a methyl doublet at 1.59 ppm, a methylene peak at 2.0 to 2.5 ppm and an absorption at 3.3 ppm adjacent to an anomeric proton. When Fortimicin B is hydrolyzed with 6N HCl and subjected to thin layer chromatography, a spot is observed at the same position as that of purpurosamine B, an aminosugar component in another antibiotic namely, Gentamicin $C_2$. Thus, from the foregoing and the mass spectrum which is discussed hereinbelow, a monoglycoside part of Fortimicin B is believed to be purpurosamine B as represented below.

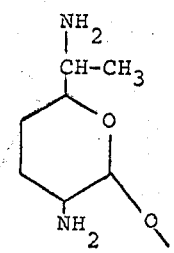

Figure 4:
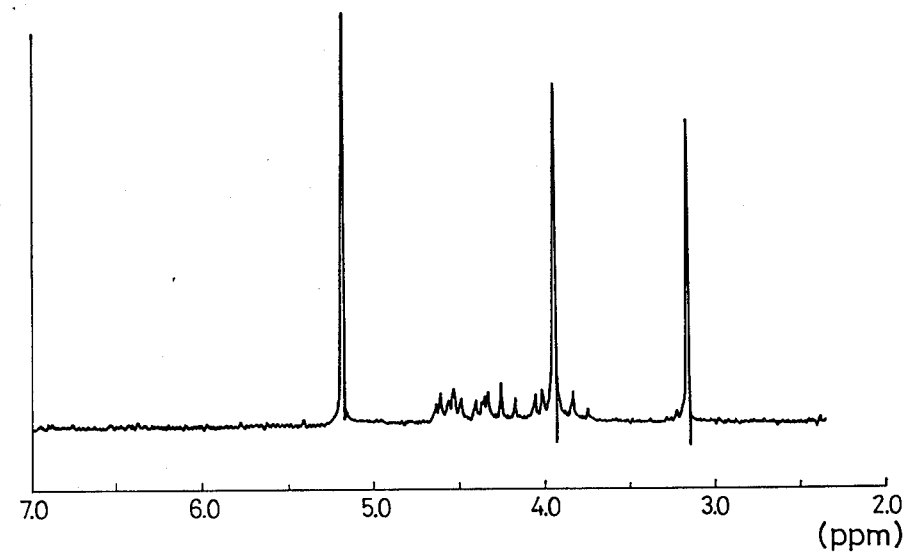
FIg. 4 is the nuclear magnetic resonance spectrum of the aminocyclitol part of Fortimicin B.

FIG. 4 illustrates the NMR spectrum of an aminocyclitol part obtained by the hydrolysis of Fortimicin B. As is apparent from the figure, the spectrum has singlet peaks at 3.17 ppm and 3.95 ppm, which show the presence of an N-methyl group and that of an O-methyl group, respectively.

Figure 5:
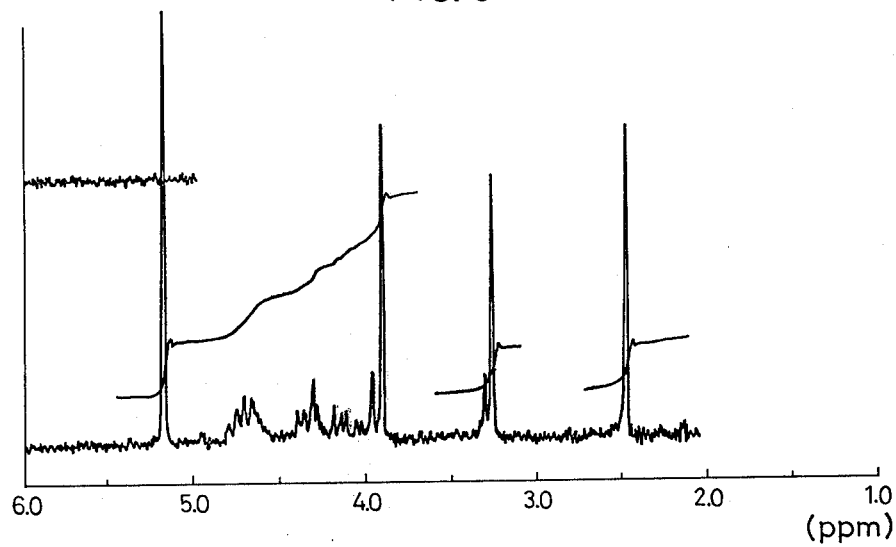
FIG. 5 is the nuclear resonance spectrum of the N-acetyl derivative of the aminocyclitol part of Fortimicin B.

FIG. 5 illustrates the NMR spectrum of the N-acetyl derivative of the aminocyclitol part. The single peak at 2.48 ppm shows the presence of an N-acetyl group, i.e., the presence of two nitrogen in the aminocyclitol part.

The results of mass spectrometry of Fortimicin B are as follows:

349.2442, 331.2099, 286.1762, 235.1297, 207.1338 143.1184, 126.0916, 100.0768, 97.0890, 88.0752, 87.0669, 96.0596, 82.0642, 72.0440, 70.0646, 56.0497, 44.0499 With regard to the above data of mass spectrometry, it is believed that the values are indicative of the $M^{+1}$ state. That is, the induced positive charge to the molecule is the result of the addition of a hydrogen nucleus rather than the more common loss of an electron. Therefore, each value is higher by a factor of 1 than the true value. From this data, it is apparent that the value of the molecular ion $M^{+1}$ is m/e 349, and that of $M^{+1} - H_2O$ is m/e 331. Additionally, the value m/e 143 indicates the presence of purpurosamine B.

The N-acetyl derivative of the aminocyclitol part obtained by the hydrolysis of Fortimicin B has a molecular ion of $M^{+1}$ of m/e 249, and also $M^{+1} - H_2O$ of m/e 231, $M^{+1} - 2H_2O$ of m/e 213 and $M^{+1} - CH_3OH$ of m/e 217. Accordingly, it is thus determined to have the molecular formula $C_{10}H_{20}N_2O_5$.

From the NMR spectrum and mass spectrum data, the aminocyclitol part of Fortimicin B is considered to have an O-methyl group, an N-methyl group, 3-OH groups and an amino group. This analysis is supported by the finding that when Fortimicin B is oxidized with periodic acid, two moles of periodic acid is consumed per one molecule of Fortimicin B. Additionally, when the antibiotic is acetylated by acetic anhydride and then treated with periodic acid, consumption of periodic acid by the N-acetyl-molecule is zero.

From the foregoing, Fortimicin B is believed to have the following structural formula:

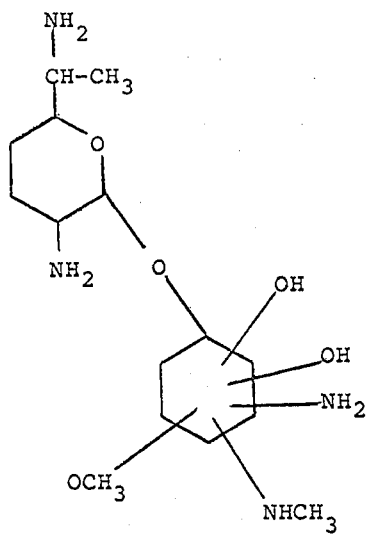

With regard to the above structural formula, and particularly the aminocyclitol part, the radicals are indicated as floating. Although the presence of the particular radicals has been confirmed, the positioning thereof has not as yet been determined.

The free base of Fortimicin B is very soluble in water, soluble also in methanol and slightly soluble in ethanol, but insoluble in such organic solvents as chloroform, benzene, ethyl acetate, butyl acetate, ethyl ether, petroleum ether, n-hexane, etc.

With regard to color tests, Fortimicin B gives positive reactions in the ninhydrin test and potassium permanganate test, and negative reactions in the Sakaguchi test, Elson-Morgan's test and biuret test.

The Rf values of Fortimicin B obtained from paper chromatography and thin layer chromatography using various developers are shown in the following Tables 3, 4 and 5. These values are compared with the Rf values of various similar antibiotics developed in the same manner.

Table 3

Rf values of Fortimicin B in ascending paper chromatography (at 28°C)

| Developer | Rf Value | Developing period (hour) |
|---|---|---|
| 20% (w/v) Ammonium chloride | 0.85 | 3 |
| Water-saturated n-butanol | 0.00 | 15 |
| n-Butanol-acetic acid-water (3:1:1) | 0.09 | 15 |
| Water-saturated ethyl acetate | 0.00 | 4 |
| Water-saturated n-butanol containing 2% (w/v) p-toluene-sulfonic acid and 2% (V/V) piperidine | 0.07 | 15 |

Table 4

Rf values of Fortimicin B and Gentamicin C complex in silica gel thin layer chromatography (developed at room temperature for 3 hours)

| Developer* | Antibiotic | Rf Value |
|---|---|---|
| I | Fortimicin B | 0.80 |
| I | Gentamicin C complex | 0.71 |
| II | Fortimicin B | 0.62 |
| II | Gentamicin C complex | 0.06 – 0.16 |

*Developer I: The upper layer of the mixture of chloroform, methanol and 17% aqueous ammonia (2:1:1 by volume)
Developer II: 10% Ammonium acetate and methanol (1:1 by volume).

Table 5

Rf values of known antibiotics in ascending paper chromatography using as a developer the lower layer of the mixture of chloroform, methanol and 17% aqueous ammonia (2:1:1) (developed at room temperature for 12 hours)

| Antibiotic | Rf Value |
|---|---|
| Streptomycin A | 0.02 |
| Streptomycin B | 0.00 |
| Bluensomycin | 0.01 |
| Ribostamycin | 0.00 |
| Lividomycin A | 0.00 |
| Lividomycin B | 0.03 |
| Lividomycin D | 0.02 |

Table 5-continued

Rf values of known antibiotics in ascending paper chromatography using as a developer the lower layer of the mixture of chloroform, methanol and 17% aqueous ammonia (2:1:1) (developed at room temperature for 12 hours)

| Antibiotic | Rf Value |
| --- | --- |
| Spectinomycin | 0.45 |
| Kasugamycin | 0.01 |
| Butirosin A | 0.00 |
| Butirosine B | 0.01 |
| Hygromycin B | 0.02 |
| Destomycin A | 0.03 |
| Gentamicin A | 0.00 |
| Gentamicin B | 0.00 |
| Gentamicin $C_{1a}$ | 0.18 |
| Gentamicin $C_1$ | 0.59 |
| Gentamicin $C_2$ | 0.38 |
| Sisomicin | 0.18 |
| Neomycin A | 0.00 |
| Neomycin B | 0.03 |
| Neomycin C | 0.00 |
| Antibiotic No. 460 | 0.01 |
| Kanamycin A | 0.02 |
| Kanamycin B | 0.01 |
| Kanamycin C | 0.02 |
| Paromomycin | 0.00 |
| Nebramycin complex | 0.01 |
| Tobramycin | 0.02 |
| Aparmycin | 0.02 |
| XK-62-2* | 0.49 |
| Fortimicin B | 0.65 |

*A new antibiotic disclosed in U.S. Pat. No. Application Serial No. 364,058; Filed, May 25, 1973.

The antibacterial spectra by agar dilution method of Fortimicin B against various microorganisms is shown in the following Table 6.

Table 6

| Microorganism tested | Minimum inhibitory concentration ($\gamma$/ml) |
| --- | --- |
| Streptococcus faecalis ATCC 10541 | >416.5 |
| Staphylococcus aureus ATCC 6538P | 6.6 |
| Staphylococcus aureus KY 8942 (resistant to kanamycin, paromomycin and streptomycin) | 104.2 |
| Staphylococcus aureus KY 8950 (resistant to streptomycin, tetracycline, penicillin and sulfonamide) | 52.1 |
| Staphylococcus aureus KY 8953 (resistant to streptomycin, kanamycin, paromomycin, tetracycline, neomycin, kanamycin B and erythromycin) | 26.1 |
| Staphylococcus aureus KY 8956 (resistant to streptomycin, paromomycin, tetracycline, erythromycin and oleandomycin) | 0.83 |
| Staphylococcus aureus KY 8957 (resistant to chloramphenicol, streptomycin, kanamycin B, tetracycline and paromomycin) | 1.65 |
| Bacillus subtilis No. 10707; KY 4273 | 104.2 |
| Bacillus cereus ATCC 9634 | 104.2 |
| Bacillus cereus var. mycoides ATCC 9463 | 104.2 |
| Klebsiella pneumoniae ATCC 10031 | 26.1 |
| Escherichia coli ATCC 26 | 13.1 |
| Escherichia coli KY 8302 (resistant to chloramphenicol, streptomycin, kanamycin, paromomycin, tetracycline and spectinomycin) | 208.3 |
| Escherichia coli KY 8310 (resistant to chloramphenicol, streptomycin, kanamycin, gentamicin, kanamycin B, parmomycin, tetracycline and spectinomycin) | 52.1 |
| Escherichia coli KY 8314 (resistant to streptomycin) | 26.1 |
| Escherichia coli KY 8315 (resistant to streptomycin, kanamycin, paromomycin and neomycin) | 26.1 |
| Escherichia coli KY 8327 (resistant to kanamycin, gentamicin, sisomicin and tobramycin) | 13.1 |
| Escherichia coli KY 8331 (resistant to kanamycin, ribostamycin, neomycin, paromomycin and lividomycin) | 1.65 |
| Escherichia coli KY 8332 (resistant to kanamycin and tobramycin) | 3.3 |

Table 6-continued

| Microorganism tested | Minimum inhibitory concentration ($\gamma$/ml) |
| --- | --- |
| Pseudomonas aeruginosa BMH No. 1 | 208.3 |
| Proteus vulgaris ATCC 6897 | 26.1 |
| Shigella sonnei ATCC 9290 | 52.1 |
| Salmonella typhosa ATCC 9992 | 13.1 |

It is evident from the above that Fortimicin B has an antibacterial activity against various Gram-positive and Gram-negative bacteria, and also has an antibacterial activity against *Staphylococcus aureus* and *Escherichia coli*, which are resistant to various known antibiotics. In view of the wide range of antibacterial spectrum and the characteristic structure, Fortimicin B is an antibiotic useful for a surface antibacterial agent. Fortimicin B also is considered to be useful as a starting material for synthesizing various derivatives by chemical modification.

A comparison of Fortimicin B with other antibiotics illustrates its novelty. As water-soluble, basic antibiotics produced by microorganisms of the genus Micromonospora having a wide range of antibacterial spectrum, there are known, for example, gentamicin [M. J. Weinstein et al: Antimicrobial Agents and Chemotherapy 1963, 1 and D. J. Cooper et al: J. Infect. Dis., 119, 342 (1969)]; antibiotic No. 460 (Japanese Patent Publication No. 16153/71); sisomicin [M. J. Weinstein et al: J. Antibiotics, 23, 551, 555, 559 (1970)]; XK-62-2 (U.S. patent application Ser. No. 364,058, filed May 25, 1973). However, as is evident from Tables 4 and 5, the Rf values of Fortimicin B in silica gel thin layer chromatography and paper chromatography are clearly distinguished from those of the A, B, $C_{1a}$, $C_2$ and $C_1$ components of gentamicin, antibiotic No. 460, sisomicin and XK-62-2. Even in comparison of water-soluble basic aminoglycoside antibiotics or constituents similar to those of Fortimicin B or its constituents, such as neomycin A (neamine), paromamine, gentamine, etc., the latter antibiotics have deoxystreptamine as a constituent, whereas Fortimicin B has no deoxystreptamine, and thus these antibiotics are clearly different. Furthermore, the chemical structure of Fortimicin B clearly distinguishes it from the other known antibiotics.

Since Fortimicin B contains basic groups it can exist in the form of acid addition salts. Accordingly, the present invention contemplates the pharmaceutically non-toxic acid addition salts of the antibiotic (i.e., the amine salts) including the mineral acid addition salts such as the hydrochloride, hydrobromide, hydroiodide, sulfate, sulfamate and phosphate and the organic acid addition salts such as the maleate, acetate, citrate, oxalate, succinate, benzoate, tartrate, fumarate, malate, mandelate, ascorbate and the like.

Practice of certain specific embodiments of the invention is illustrated by the following representative examples:

EXAMPLE 1

In this example, *Mircomonospora olivoasterospora* (ATCC 21819) (FERM-P No. 1560) is used as a seed strain and is initially cultured in a first seed medium containing 2% glucose, 0.5% peptone, 0.5% yeast extract and 0.1% calcium carbonate (pH 7.2 before sterilization) by inoculating one loopful of the seed strain into 10 ml of the seed medium in a 50 ml large test tube. Culturing is carried out at 30°C for 5 days with shaking. Ten ml of the seed culture broth is then inoculated into 30 ml of a second seed medium in a 250 ml Erlenmeyer flask. The composition of the second seed medium is the same as that of the first seed medium. The second seed culturing is carried out at 30°C for two days with shaking.

Then 30 ml of the second seed culture broth is inoculated into 300 ml of a third seed medium in a 2 L Erlenmeyer flask provided with baffles. The composition of the third seed medium is the same as that of the first seed medium. The third seed culturing is carried out at 30°C for 2 days with shaking. Thereafter, 1.5 L of the third seed culture broth (corresponding to the content of five flasks) is inoculated into 15 L of a fourth seed medium in a 30 L glass jar fermenter. The composition of the fourth seed medium is the same as that of the first seed medium. Culturing in the jar fermenter is carried out at 30°C for two days with aeration and stirring (revolution: 350 r.p.m.; aeration: 15 L/min). Finally, 15 L of the fourth seed culture broth is inoculated into 150 L of a main fermentation medium in a 300 L stainless steel fermenter. The main fermentation medium comprises: 4% starch, 2% soybean meal, 1% corn steep liquor, 0.05% $K_2HPO_4$, 0.05% $MgSO_4.7H_2O$, 0.03% KCl and 0.1% $CaCO_3$ (pH 7.5 before sterilization). Culturing in the fermenter is carried out at 30°C for 4 days with aeration and stirring (revolution: 150 r.p.m.; aeration: 80 L/min).

The resulting fermentation broth is adjusted to a pH of 2.5 with concentrated sulfuric acid, and stirred for 30 minutes. Then, about 7 kg of a filter aid, Radiolite No. 600 (product of Showa Kagaku Kogyo Co., Ltd. Japan) is added thereto and the microbial cells are removed by filtration. The filtrate is adjusted to a pH of 7.5 with 6N sodium hydroxide and passed through a column packed with about 20 L of a cation exchange resin, Amberlite IRC-50 (ammonia form), and the effluent is discarded. Active substances are adsorbed on the resin. After washing the resin with water, the adsorbed active substances are eluted out with 1N aqueous ammonia. Activity of the eluate is determined by a paper disc method, using an agar plate of *Bacillus subtilis* No. 10707. The active fractions are collected and the mixture is concentrated to about 1 L under reduced pressure. The concentrate is passed through a column packed with 500 ml of an anion exchange resin, Dowex 1 × 2 ($OH^-$ form), and then the column is washed with about 2 L of water, whereby impurities are removed. The active substances are eluted out with water. The thus obtained active fractions are collected, and concentrated to about 100 ml under reduced pressure and then passed through a column packed with about 50 ml of active carbon powder whereby the active substances are adsorbed onto the carbon powder. The column is washed with water and the effluent and the washing water are discarded. Then, the adsorbed active substances are eluted out with 0.2N sulfuric acid. Activity of the eluate is determined by the paper disc method using *Bacillus subtilis*, and the active fractions are collected. The thus obtained fractions are passed through a column of Dowex 44 ($OH^-$ form). The active substances are then eluted out with water and collected and concentrated to about 50 ml. The thus obtained concentrate is lyophilized, whereby a crude powder containing Fortimicin B is obtained. The yield of the crude powder is about 32 g. The crude powder exhibits an activity of 680 unit/mg (the activity of 1 mg of a pure product corresponds to 1000 units).

The thus obtained crude powder including Fortimicin B is placed uniformly on the upper end of a glass column tightly packed with about 1 L of silica gel. The silica gel column is prepared by first suspending the silica gel in a solvent comprising chloroform, isopropanol and 17% aqueous ammonia (2:1:1 by volume). The suspension is packed in the column as a uniform layer, and then well washed with the same solvent. After placing the crude powder at the head of the column, elution is carried out with the same solvent which is gradually poured into the column from its top; and, thereafter, the elution is carried out at a flow rate of about 50 ml/hour. The eluate is collected in fractions of 20 ml each, and the activity of each fraction is determined by the paper disc method. The active fractions are subjected to paper chromatography, and the fractions containing Fortimicin B are collected. Fortimicin B is the active component initially eluted from the column. While the elution is continued other by-products, including the aforementioned active substance XK-70-1, which are contained in the crude powder, are eluted. The fractions containing Fortimicin B are collected and concentrated under reduced pressure to completely remove the solvent. The concetrate is then dissolved in a small amount of water and after freeze-drying the solution, about 1.5 g purified preparate of Fortimicin B (free base) is obtained. The activity of the preparate is about 965 unit/mg.

EXAMPLE 2

In this example, the strain of Example 1 is used as the seed strain, and a seed medium containing 1% glucose, 1% soluble starch, 0.1% yeast extract, 0.5% peptone and 0.1% calcium carbonate is used as the seed media in four stages of seed culturing. The four seed culturings are carried out in the same manner as in Example 1.

Then, 15 L of the fourth seed culture broth is inoculated into 150 L of a fifth seed medium of the same composition as the previous seed media in a 300 L stainless steel fermenter. Culturing in the fermenter is carried out at 30°C for two days with aeration and stirring. Then, 150 L of the fifth seed culture broth is inoculated into 1200 L of a main fermentation medium in a 2000 L fermentation tank. The main fermentation medium comprises: 4% soluble starch, 3% Ebios (trade name, dried yeast powders, produced by the Tanabe Pharmaceutical Co., Japan), 0.05% $K_2HPO_4$, 0.05% $MgSO_4.7H_2O$, 0.03% KCl and 0.1% $CaCO_3$.

The main fermentation is carried out at 37°C for 4 days with aeration and stirring. The production of active substances reaches almost maximum after 96 hours from the start of culturing.

After the completion of the culturing, separation and purification of Fortimicin B are carried out in the same manner as in Example 1, whereby about 34 g of purified preparate having an activity of about 950 unit/mg is obtained.

EXAMPLE 3

In this example, *Micromonospora olivoasterospora* Mm 744, KY 10067, ATCC 31009 (FERM-P No. 2193) is used as a seed strain. A medium containing 2% glucose, 0.5% peptone, 0.3% yeast extract and 0.1% calcium carbonate (pH 7.2 before sterilization) is used as the seed medium for the first through fourth seed culturing carried out in the same manner as in Example 1.

Then 15 L of the fourth seed culture broth is inoculated into 150 L of a main fermentation medium in a 300 L stainless steel fermenter. The main fermentation medium comprises: 2% soluble starch, 0.5% soybean meal, 2% glucose, 1% corn steep liquor, 1% yeast extract, 0.05% $K_2HPO_4$, 0.05% $MgSO_4 \cdot 7H_2O$, 0.03% KCl and 0.1% $CaCO_3$ (pH 7.0 before sterilization). Culturing is carried out at 30°C for 4 days with aeration and stirring (revolution: 150 r.p.m.; aeration 80 L/min).

After the completion of culturing, separation and purification of Fortimicin B are carried out in the same manner as in Example 1, whereby about 1.3 g of purified preparate having an activity of about 962 unit/mg is obtained.

EXAMPLE 4

In this example, *Micromonospora olivoasterospora* MK-80, KY 11055, ATCC 31010 (FERM-P No. 2192) is used as a seed strain. A medium containing 1% glucose, 1% soluble starch, 0.5% yeast extract, 0.5% peptone and 0.1% calcium carbonate (pH 7.0 before sterilization) is used as the seed medium for the first through fifth seed culturing carried out in the same manner as in Example 2.

Then 150 L of the fifth seed culture broth is inoculated into 1200 L of a main fermentation medium in a 2000 L fermenter. The main fermentation medium has the same composition as that in Example 1. The main culturing is carried out at 30°C for 4 days with aeration and stirring.

After the completion of culturing, separation and purification of Fortimicin B are carried out in the same manner as in Example 1, whereby about 38 g of purified preparate having an activity of about 972 unit/mg is obtained.

What is claimed is:
1. A composition of matter having antibiotic activity characterized by:
   a. molecular weight of 348;
   b. molecular formula of $C_{15}H_{32}N_4O_5$;
   c. an ultraviolet absorption spectrum essentially as shown in FIG. 1;
   d. an infrared absorption spectrum essentially as shown in FIG. 2; and
   e. a nuclear magnetic reasonance spectrum essentially as shown in FIG. 3. said composition of matter being Fortimicin B.

2. A pharmaceutically acceptable, non-toxic acid addition salt of the composition of matter of claim 1, said acid addition salt being selected from the group consisting of the hydrochloride, hydrobromide, hydroiodide, sulfate, sulfamate, phosphate, maleate, acetate, citrate, oxalate, succinate, benzoate, tartrate, fumarate, malate, mandelate and ascorbate.

3. A process for producing the antibiotic Fortimicin B which comprises culturing a microorganism selected from the group consisting of *Micromonospora olivoasterospora* ATCC 21819, *Micromonospora olivoasterospora* ATCC 31009 and *Micromonospora olivoasterospora* ATCC 31010 in a nutrient medium containing assimilable sources of carbon and nitrogen at 25° to 40°C. and at about neutral pH until substantial antibacterial activity is detected in the culture liquor and thereafter isolating Fortimicin B.

* * * * *